United States Patent [19]

Thenappan et al.

[11] Patent Number: 5,629,460
[45] Date of Patent: May 13, 1997

[54] PROCESS FOR THE PREPARATION OF 1,1,1, 3,3,3-HEXAFLUORO-2-PROPANONE

[75] Inventors: Alagappan Thenappan, Cheektowaga; Michael Van Der Puy, Amherst; Richard Eibeck, Orchard Park, all of N.Y.

[73] Assignee: AlliedSignal Inc., Morris County, N.J.

[21] Appl. No.: 686,682

[22] Filed: Jul. 26, 1996

[51] Int. Cl.$^6$ ............................................. C07C 21/18
[52] U.S. Cl. ...................... 570/134; 570/234; 570/255; 568/407
[58] Field of Search ........................... 568/407; 570/134, 570/234, 255

[56] References Cited

PUBLICATIONS

U.S.S.R. From: Izobreteniya; (35)302 —Vilenchik, Ya. M. et al. 1995.
Fluorine Chemistry Reviews; 1(1), 145–196 —Krespan, C.G. et al. 1967.

*Primary Examiner*—Gary Geist
*Assistant Examiner*—Sreeni Padmanabhan
*Attorney, Agent, or Firm*—Jay P. Friedenson

[57] ABSTRACT

A vapor phase process for the preparation of fluorinated ketones, such as 1,1,1,3,3,3-hexafluoro-2-propanone via oxidation of hydrofluorocarbons, such as 1,1,1,3,3,3-hexafluoropropane, with an oxidizing agent and elemental fluorine at temperatures ranging from 50° C. to 300° C. and residence times ranging from 2 to 60 seconds.

16 Claims, No Drawings

PROCESS FOR THE PREPARATION OF 1,1,1, 3,3,3-HEXAFLUORO-2-PROPANONE

Field of the Invention

This invention relates to a vapor phase process for the preparation of fluorinated ketones, such as, 1,1,1,3,3,3-hexafluoro-2-propanone. In particular, the present invention provides a method for preparing 1,1,1,3,3,3-hexafluoro-2propanone via oxidation of 1,1,1,3,3,3-hexafluoropropane with an oxidizing agent and elemental fluorine ($F_2$).

BACKGROUND OF THE INVENTION 1,1,1,3,3,3-hexafluoro-2-propanone (i.e., hexafluoroacetone or HFA) is used as a starting material to prepare hexafluoroisopropylidene (HFIP) bridged compounds, which are used as monomers in the synthesis of high performance polymers, specialty coatings and pharmaceutical intermediates. Incorporation of hexafluoroisopropylidene moiety into the polymer chain is known to influence the solubility, processability, oxidative stability and electrical properties.

There are a number of methods to prepare HFA in the literature [Krespan and Middleton, *J. Fluorine Chem. Rev.* 1967, 1, 145] each having certain limitations. For example, in the halogen-exchange fluorination of hexachloroacetone using anhydrous HF and chromium oxide catalyst, the exchange of last chlorine to fluorine is very difficult and the intermediate pentafluorochloro-2-propanone is highly toxic. Epoxidation of hexafluoropropene to hexafluoropropene oxide followed by isomerization to HFA with liquid HF as a solvent requires the use of expensive corrosion-resistant reactors. Finally, perfluoroisobutylene, used as a starting material to prepare HFA is extraordinarily toxic.

The preparation of HFA from 1,1,1,3,3,3-hexafluoropropane (i.e., $CF_3CH_2CF_3$ or HFC-236fa) has several advantages over other methods. The starting material, HFC-236fa, can be readily prepared in high yield from carbon tetrachloride and vinylidene chloride according to U.S. Pat. No. 5,395,997, and the process is amenable to commercial scale-up. The by-product produced in the oxidation step of this process is water and the process can be operated continuously. The present invention relates to a process for the preparation of HFA which can be economically and ecologically superior to existing processes.

1,1,1,3,3,3-Hexafluoropropane (i.e., HFC-236fa) has an atmospheric life time of 265 years indicating a slow reaction with hydroxyl radicals. It is relatively inert to chlorine and bromine radicals too. For example, Henne et al., [*J. Amer. Chem. Soc.*, 67, 1906 (1945)] have reported that HFC-236fa resists chlorination completely in bright sunlight and bromination of HFC-236fa with elemental bromine at 550°–585° C. [L. H. Beck's *Thesis, University Microfilms, Inc.*, The Ohio State University, 1959, p 23] yielded only small amount of 2-bromo-1,1,1,3,3,3hexafluoropropane (i.e., $CF_3CHBrCF_3$). Reaction of HFC-236fa with elemental fluorine is not known. Poor reactivity of HFC-236fa towards chlorine and bromine is attributed to heavy shielding of the hydrogens located on the central carbon of HFC-236fa by two adjacent trifluoromethyl groups. The same shielding effect is expected to prevent any radical attack on those hydrogens including fluorine.

Fluorine is different from other halogens in that fluorine-fluorine bond energy is relatively low and carbon-fluorine and hydrogen-fluorine bond energies are very high. Reactions with fluorine require very low activation energies and fluorine sensitized oxidation and halogenation of unsaturated olefins are known in the literature. Miller and co-workers [*J. Amer. Chem. Soc.*, 1956, p 2793] have accumulated enough evidence to show the role of fluorine as an initiator in the oxidation of trichloroethylene and tetrachloroethylene. The use of fluorine to oxidize fluorine containing compounds such as hydrofluorocarbons and hydrochlorofluorocarbons has not been reported. In an attempt to prepare the titled compound, HFC-236fa was reacted with air and fluorine in a fluidized bed reactor and the reaction yielded the desired HFA and its hydrate in high selectivity and good conversion. The oxidation of HFC-236fa in the presence of fluorine provides a route to producing 1,1,1,3,3,3-hexafluoro-2propanone which is cleaner and cheaper than the existing methods.

SUMMARY OF THE INVENTION

The present invention provides a process for the preparation of 1,1,1,3,3,3-hexafluoro-2-propanone by oxidation of 1,1,1,3,3,3-hexafluoropropane. The vapor phase process includes contacting 1,1,1,3,3,3-hexafluoropropane with air and fluorine at a temperature of from about 50° C. to about 300° C.

DETAILED DESCRIPTION OF THE INVENTION

The present invention provides a process to prepare 1,1,1,3,3,3-hexafluoro-2-propanone by gas phase oxidation of 1,1,1,3,3,3-hexafluoropropane with air in the presence of fluorine as the initiator. The process includes the contacting of HFC-236fa with fluorine and an oxidizing agent in a fluidized bed reactor in the presence of a particulate phase at temperatures ranging from 50° C.–300° C.

The reactor used in the oxidation process, according to the present invention, may be any reactor known in the art, including any simple tubular reactor constructed of a metal resistant to attack by reactants. Preferably the reactor is constructed with either stainless steel or copper. The most preferred metal for the reactor is stainless steel. Since reactions involving elemental fluorine are highly exothermic, the reactor is usually packed with a material such as alumina, copper metal turnings, or the like, generally known in the art to provide favorable mixing of the gas streams, good dissipation of heat, and possibly even an active surface for heterogeneous reactions. Preferably the reactor is packed with either alumina or copper metal turnings with the most preferred packing being alumina. The size of the alumina (particulate phase) ranges from 120 to 320 mesh, with preferred particle size being 180 to 220 mesh. The packing materials used for the oxidation process are commercially available.

The hydrofluorocarbons to be oxidized according to the present invention have the general formula: $[F(CF_2)n]2CH_2$, wherein n=1–5. Examples of such hydrofluorocarbons include: $(CF_3)_2CH_2$, $(CF_3CF_2)_2CH_2$, $(CF_3CF_2CF_2)_2CH_2$, $(CF_3CF_2CF_2CF_2)_2CH_2$, and $(CF_3CF_2CF_2CF_2CF_2)_2CH_2$ with the most preferred hydrofluorocarbons for the oxidation being 1,1,1,3,3,3-hexafluoropropane.

The products resulting from the oxidation according to the present invention have the general formula: $[F(CF_2)n]2C(O)$, wherein n=1–5. Examples of such products include: $(CF_3)_2C(O)$, $(CF_3CF_2)_2C(O)$, $(CF_3CF_2CF_2)_2C(O)$, $(CF_3CF_2CF_2CF_2)_2C(O)$ and $(CF_3CF_2CF_2CF_2CF_2)_2C(O)$ with the most preferred product from the oxidation being 1,1,1,3,3,3-hexafluoro-2-propanone (i.e., $CF_3C(O)CF_3$, HFA).

The hydrocarbon 1,1,1,3,3,3-hexafluoropropane ($CF_3CH_2CF_3$, HFC-236fa) is commercially available and can also be prepared by the reaction of 1,1,1,3,3,3-hexachloropropane ($CCl_3CH_2CCl_3$) with HF in the presence of antimony catalyst using the procedure disclosed in U.S. Pat. No. 5,395,997.

Elemental fluorine gas used in the process is commercially available and the gas is used without any additional purification. Fluorine is usually diluted with a carrier gas to reduce the heat generated in the oxidation process and to reduce the amount of unwanted by-products as well as to adjust the overall residence time of the substrate to be oxidized in the reactor by varying the total gas flow rate. Suitable carrier gases include nitrogen, helium, argon and air. The preferred carrier gases are air and nitrogen with the most preferred carrier gas being air. Dilution of fluorine with the carrier gas is accomplished by mixing pure fluorine gas with the carrier gas in the concentration required to carry out the oxidation. The gases are allowed to mix in a tee connection and the gases entering the tee connection are measured with flow meters or rotometers of the type well known in the art.

The oxidizing agent useful in the present invention is selected from air, molecular oxygen, and mixtures of nitrogen and oxygen. Preferably the oxidizing agent is either air or mixtures of nitrogen and oxygen, with the most preferred oxidizing agent being air. The oxidizing agents useful for the present invention are commercially available.

The hydrofluorocarbons used in the present invention are either gases or liquids. For liquid hydrofluorocarbons, an inert carrier gas such as nitrogen is used to carry it into the vapor phase by purging the hydrofluorocarbon container with the carrier gas.

The oxidation process according to the present invention may be carried out either as a batch or a continuous process. However, for large scale production, the process is conducted preferably in a continuous flow system by passing vapors of carrier gas, fluorine and hydrofluorocarbon through a tubular reactor containing the particulate phase.

The oxidation process for the present invention is preferably conducted in the temperature range of about 50° C. to about 300° C. At the lower end of the temperature range, conversion of the starting material is very low, while at higher temperatures the amount of by-products increase and the selectivity is diminished. More preferably the temperature ranges from 100° C.–250° C., with the most preferable range being 150° C.–225° C. Pressure is not critical for the present invention and it is most convenient to operate the oxidation process at approximately atmospheric pressure with the only pressure above atmospheric being due to back pressure of the system. Useful residence time ranges from about 2 seconds to 100 seconds, preferably from 30–60 seconds. Residence times may be adjusted by changing the volume of the particulate phase, the reaction temperature or the total gas flow rates.

Since the role of fluorine gas is to initiate the reaction of 236fa with oxygen, the molar ratio of fluorine to hydrofluorocarbon should be kept at minimum in order to limit the amount of unwanted by-products. A useful molar ratio of $F_2$/hydrocarbon ranges from 0.01 to 3.0 with the preferable ratio being from 0.01 to 0.5.

Based on reaction stoichiometry, the required ratio of oxygen present in the oxidizing agent to hydrofluorocarbon is 1 and preferably the concentration of the oxygen be kept high to increase the conversion of the hydrofluorocarbon. Most preferred ratio of oxygen to hydrofluorocarbon ranges from 2 to 10.

The oxidation process for the present invention is preferably operated in such a way that either the fluorine conversion is high or unreacted fluorine is returned to the reactor. Similarly the process is operated in such a way that unused oxidizing agent is returned to the reactor.

The resulting oxidized compounds may be separated from the product stream via any known separation or purification method known in the art such as neutralization and distillation.

EXAMPLES

The following examples serve to illustrate the invention, but are not intended to limit the scope of the invention.

The fluidized bed reactor consisted of a vertical stainless steel pipe (2'×2" ID) which was threaded at both the ends to accept caps. A 20 micron porous disc was used at the bottom to retain the particulate phase and to distribute the entering gaseous materials. A ¼" stainless steel tube fitted at the end with a porous frit of 15 micron pores was used to introduce the organic materials. Fluorine and air were introduced through a common ¼" pipe from the bottom. The reactor was initially filled to a depth of 8" (400 ml) with 180 mesh alumina and heated with the air flow. After thermal equilibrium was reached, fluorine was introduced and finally organic was fed from the top. Reactor temperatures were monitored using thermocouples near the reaction and sample exiting zones. Fluorine flow rate to the reactor was measured with a Teledyne Hastings-Raydist, Model ST-M mass flow meter and controlled with a needle valve. Matheson rotometer and flow meters were used to measure the air and organic flow rates. The cylinder containing HFC-236fa was pressurized with nitrogen (60 psi) to facilitate the upward flow of the organic material through a check valve. Gases exiting the reactor from the top were directed through a stainless steel tube(1'×1" ID) packed with anhydrous sodium fluoride to trap HF. The HF-free vapors were then passed into a product trap consisting of a one-liter stainless steel cylinder cooled to −78° C. using dry ice/isopropyl alcohol mixture. Uncondensed gases exiting the product trap were passed through an aqueous potassium hydroxide solution. At the conclusion of the run, the fluorine and organic flows were shut off and the stainless steel cylinder containing the products was disconnected and its contents were analyzed by gas chromatography, GC-MS and NMR.

The GC analysis was performed on a Hewlett-Packard Series II 5890 Gas Chromatograph coupled with a 3396 integrator.

Example 1

The above described reactor was purged with air at the rate of 400 cc/minute and heated to 160° C. When the temperature of the reactor stabilized, fluorine was introduced at a flow rate of 40 cc/minute. After the initial exotherm subsided (~5 minutes), HFC-236fa was introduced at the flow rate of 15 g/hour. While feeding 19.6 g (129 mmoles) of HFC-236fa in one hour 20 minutes, three exiting gas samples were collected at the beginning, middle and end of the feeding of HFC-236fa and analyzed by GC, GC-MS, GC-IR and $^{19}$F NMR.

Reaction conditions, product distribution and conversion of 236fa for the three samples (entry no. 1–3) are presented in Table I. GC-MS: 166($M^+$), 69 (base peak); GC-IR: 1795(w), 1350(m), 1220(s, doublet), 975(s) and 700(m). $^{19}$F NMR [$CDCl_3$, $CFCl_3$ int. ]: −63.7 ppm(t, J=9.5 Hz, due to $\underline{C}F_3CH_2CF_3$), −76.1ppm(s, due to $\underline{C}F_3COCF_3$) and −83.1ppm(s, broad, due to $\underline{C}F_3COCF_3.xH_2O$).

Example 2

The fluidized bed reactor and procedure of Example 1 were utilized except the fluorine flow rate was reduced to 20 cc/minute. Air and 236fa flow rates were maintained at 400 cc/min. and 50 cc/min., respectively. While feeding 20.5 g(135 mmoles) 236fa in one hour 25 minutes, two gas samples were collected at the beginning (entry no. 4) and end (entry no. 5) of the organic feeding and analyzed by GC. Conversion of 236fa, reaction conditions and product distribution are summarized in Table I. This example demonstrates that oxidation of HFC-236fa to HFA can be carried out with less than stoichiometric amount of fluorine.

Example 3

The fluidized bed reactor and procedure of example 1 were utilized except the reactor was initially heated to 55° C. with an air flow of 400 cc/minute. Fluorine and 236fa flow rates were maintained at 40 cc/min. and 50 cc/min., respectively. While feeding 14.5 g(95.4 mmoles) 236fa in 45 minutes, two gas samples were collected at the beginning (entry no. 6) and end (entry no. 7) of the organic feeding and analyzed by GC. Conversion of 236fa, reaction conditions and product distribution are summarized in Table I. This example demonstrates that oxidation of HFC-236fa to HFA can be carried out at the lower end of the temperature range, viz, 50° C.–60° C., albeit in low conversion.

Example 4

The fluidized bed reactor and procedure of Example 1 were utilized except the air flow rate was increased to 600 cc/minute. F2 and 236fa flow rates were maintained at 40 cc/min. and 50 cc/min., respectively. While feeding 12.5 g(82.2 mmoles) 236fa in 30 minutes, two gas samples were collected at the beginning (entry no. 8) and end (entry no. 9) of the feeding and analyzed by GC. Conversion of 236fa, reaction conditions and product distribution are summarized in Table I. The effect of concentration of the oxidizing agent and fluorine on conversion and selectivity in the oxidation reaction is demonstrated in this example.

$[F(CF_2)n]2\ CH_2$, wherein n=1–5.

3. The process for preparation of fluorinated ketones in accordance with claim 1, wherein said fluorinated ketone has a general formula:

$[F(CF_2)n]2\ C(O)$, wherein n=1–5.

4. The process for preparation of fluorinated ketones in accordance with claim 1, wherein said oxidizing agent is selected from the group consisting of air, molecular oxygen and mixtures of nitrogen and oxygen.

5. The process for preparation of fluorinated ketones in accordance with claim 1, wherein said oxidizing agent is air.

6. The process for preparation of fluorinated ketones in accordance with claim 1, wherein said process is conducted in a reactor packed with a material selected from the group consisting of alumina and copper metal turnings.

7. The process for preparation of fluorinated ketones in accordance with claim 1, wherein said process is conducted in a reactor packed with an alumina material having a particulate phase ranging from 120 to 320 mesh.

8. The process for preparation of fluorinated ketones in accordance with claim 1, wherein said process is conducted in a reactor packed with an alumina material having a particulate phase ranging from 180 to 220 mesh.

9. The process for preparation of fluorinated ketones in accordance with claim 1, wherein said process is conducted in a vapor phase.

10. The process for preparation of fluorinated ketones in accordance with claim 1, wherein said process is conducted at temperatures ranging from about 50° C. to about 300° C.

11. The process for preparation of fluorinated ketones in accordance with claim 1, wherein said process is conducted at residence times ranging from about 2 seconds to 100 seconds.

12. The process for preparation of fluorinated ketones in accordance with claim 1, wherein a molar ratio of said $F_2$/hydrofluorocarbon is from 0.01 to 3.0.

13. The process for preparation of fluorinated ketones in accordance with claim 1, wherein a molar ratio of said oxidizing agent to said hydrofluorocarbon is from 2 to 10.

TABLE 1

| No. | Temperature (C.) Reaction zone | Temperature (C.) Exit zone | Molar ratio F2/236fa | Flow Rates (CC/min) Air | Flow Rates (CC/min) F2 | Flow Rates (CC/min) 236fa | Conv. 236fa (%) | GC Yield (area %) 236fa | GC Yield (area %) HFA | GC Yield (area %) HFA hydrate | GC Yield (area %) Other pdts. |
|---|---|---|---|---|---|---|---|---|---|---|---|
| 1 | 165 | 153 | 0.94 | 389 | 38 | 50 | 84.2 | 15.8 | 27.3 | 51.3 | 5.6 |
| 2 | 169 | 154 | 0.94 | 388 | 38 | 50 | 69.7 | 30.3 | 56.1 | 13.1 | 0.5 |
| 3 | 177 | 169 | 0.94 | 389 | 38 | 50 | 11.0 | 89.1 | — | 10.7 | 0.2 |
| 4 | 168 | 160 | 0.48 | 383 | 19.3 | 50 | 47.1 | 52.9 | 16.5 | 27.6 | 3.0 |
| 5 | 191 | 174 | 0.48 | 376 | 19.4 | 50 | 19.0 | 81.0 | 8.5 | 8.6 | 1.9 |
| 6 | 53 | 52 | 0.94 | 390 | 39 | 50 | 4.5 | 95.5 | 3.8 | 0.4 | 0.4 |
| 7 | 60 | 58 | 0.94 | 390 | 39 | 50 | 0.1 | 99.9 | 0.01 | — | 0.08 |
| 8 | 159 | 156 | 1.19 | 600 | 40 | 45 | 46.3 | 53.7 | 21.4 | — | 24.9 |
| 9 | 155 | 157 | 1.79 | 600 | 60 | 50 | 65.3 | 34.8 | 58.6 | — | 6.7 |

What is claimed is:

1. A process for preparation of fluorinated ketones comprising: contacting an hydrofluorocarbon with an oxidizing agent and fluorine to produce said fluorinated ketones.

2. The process for preparation of fluorinated ketones in accordance with claim 1, wherein said hydrofluorocarbon has a general formula:

14. A process for preparation of fluorinated ketones comprising: contacting 1,1,1,3,3,3-hexafluoropropane with air and fluorine, wherein a molar ratio of said fluorine to said 1,1,1,3,3,3-hexafluoropropane is from 0.1 to 0.5 and a molar ratio of said air to said 1,1,1,3,3,3-hexafluoropropane is from 2 to 10.

15. A process for preparation of fluorinated ketones in accordance with claim 14, wherein said process takes place in a fluidized bed reactor having an alumina packing, and a temperature ranging from 150° C. to 225° C.

16. A process for preparation of fluorinated ketones in accordance with claim 14, wherein said process has a residence time of from 30–60 seconds thereby producing said 1,1,1,3,3,3- hexafluoro-2-propanone.

* * * * *